United States Patent [19]
Franz et al.

[11] 4,179,476
[45] Dec. 18, 1979

[54] SEMI-CONTINUOUS PROCESS FOR OBTAINING AMINO COMPOUNDS

[75] Inventors: Gerhard Franz, Frick, Switzerland; Georg Halfter, Wyhlen, Fed. Rep. of Germany; Walter Jaeckle; Fritz Mindermann, both of Grenzach, Fed. Rep. of Germany

[73] Assignee: Ciba-Geigy Corporation, Ardsley, N.Y.

[21] Appl. No.: 854,443

[22] Filed: Nov. 23, 1977

Related U.S. Application Data

[63] Continuation of Ser. No. 706,370, Jul. 19, 1976, abandoned.

[30] Foreign Application Priority Data

Jul. 31, 1975 [DE] Fed. Rep. of Germany ....... 2534176

[51] Int. Cl.² ..................... C07C 85/11; C07C 143/56
[52] U.S. Cl. .................................. 260/706; 260/508; 260/509; 260/510; 260/580
[58] Field of Search .............. 260/510, 508, 509, 580, 260/581; 568/705, 706

[56] References Cited

U.S. PATENT DOCUMENTS

| | | | |
|---|---|---|---|
| 2,179,919 | 11/1939 | Carr | 260/580 |
| 2,784,220 | 3/1957 | Spiegler | 260/580 |
| 2,875,243 | 2/1959 | Roos et al. | 260/505 |
| 3,350,441 | 10/1967 | Leightle | 260/508 |
| 3,989,743 | 11/1976 | Braden | 260/510 |

OTHER PUBLICATIONS

Groggins, "Unit Processes in Organic Synthesis," pp. 134–165.
Houben-Weyl, "Methoden der Organischen Chemie, vol. 11/1 pp. 394–401, 1957.

*Primary Examiner*—Werren B. Lone
*Attorney, Agent, or Firm*—Prabodh I. Almaula

[57] ABSTRACT

A semi-continuous process for manufacturing aliphatic or aromatic amino compounds by reduction of the corresponding nitro compounds in an acid medium with iron which is etched with acids or salts is provided.

8 Claims, 1 Drawing Figure

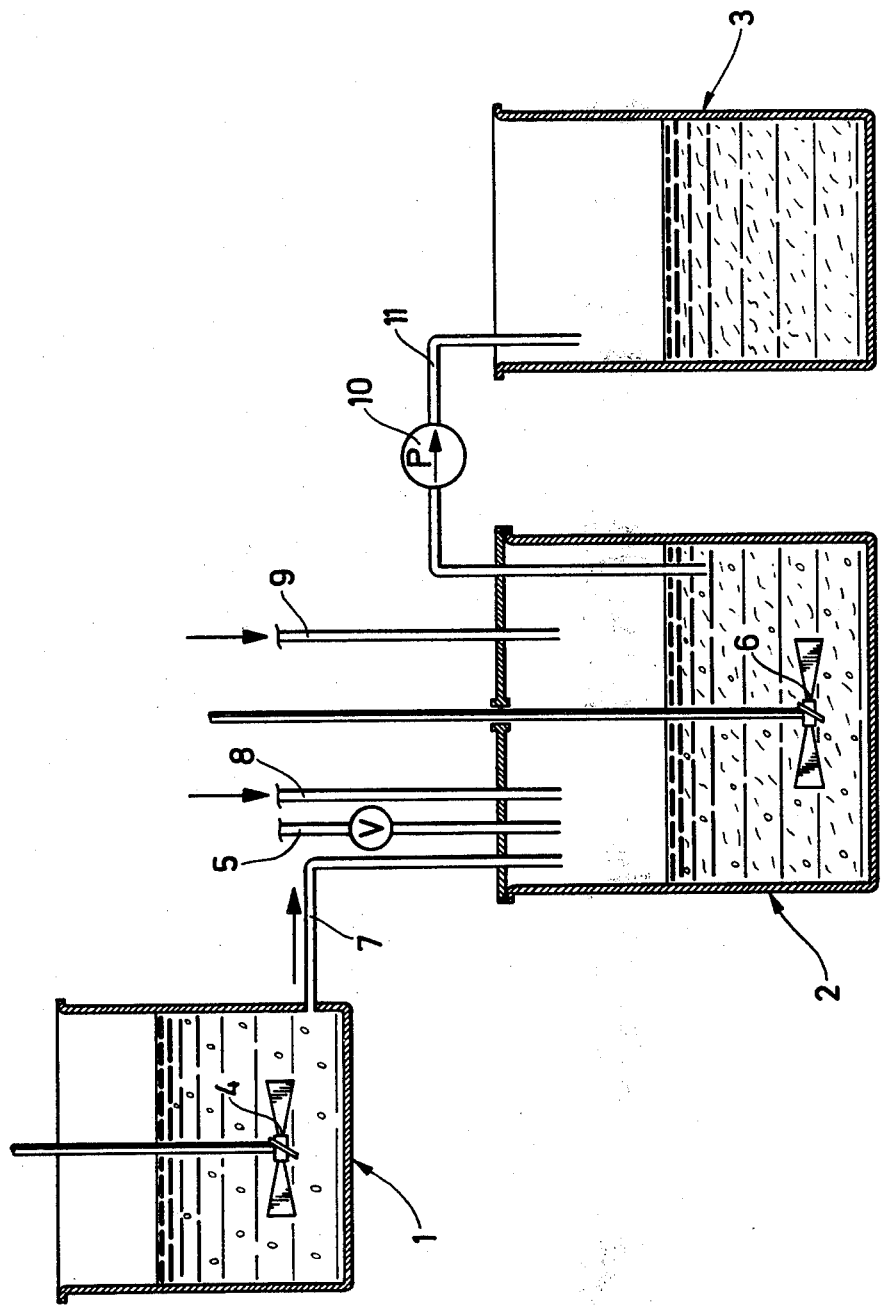

SEMI-CONTINUOUS PROCESS FOR OBTAINING AMINO COMPOUNDS

This is a continuation of application Ser. No. 706,370, filed on July 19, 1976, now abandoned.

The present invention provides a semi-continuous process for obtaining amino compounds by reduction of nitro compounds with iron in weakly acid medium.

It is known to obtain amino compounds by reduction of nitro compounds with iron in weakly acid medium. Considerable disadvantages of this process—known as the Béchamp reduction—are, on the one hand, the difficulties involved in carrying it out fully continuously, and on the other, the necessity of using a substantial excess of iron. Unconsumed iron cannot be reused, because it is mixed with the precipitated iron oxide and other impurities (inactivated). A semi-continuous process has now been found which does not have these disadvantages.

The semi-continuous process of this invention for obtaining aliphatic or aromatic amino compounds by reduction of the corresponding nitro compounds at elevated temperature and in acid medium with iron which is etched with acid or salts, comprises introducing a less than stoichiometric amount of an aqueous solution or dispersion of an aliphatic or aromatic nitro compound, at temperatures between 50° and 110° C., into a reaction vessel containing the etched iron, separating the still acid iron oxide/water/amino compound mixture obtained from unconsumed iron, introducing a further less than stoichiometric amount of nitro compound into the reaction vessel containing the unconsumed iron, which may be replenished with fresh iron if appropriate, freeing the still acid iron oxide/water-/amino compound mixture obtained once more from unconsumed iron etc., and treating the separated water-/iron oxide/amino compound mixtures in known manner to obtain the amino compound.

The nitro compounds to be reduced can contain one or more nitro groups. Preferably those nitro compounds are reduced which yield amino compounds which are water-soluble under the reaction conditions.

In a particularly preferred embodiment of the process according to the invention, aromatic nitro compounds are used, for example nitrobenzene, 2-nitro-4-methylsulphonyl-phenol, 2-nitro-2'-sulpho-4,4'-dichloro-diphenyl ether, 4,4'-dinitrostilbene-2,2'-disulphonic acid, nitrobenzenedisulphonic acid-2,5, and 3-nitrobenzenesulphonic acid.

The reduction according to the present invention is preferably carried out at a temperature between 90° and 100° C.

A low molecular fatty acid, in particular acetic acid, is used as acid. However, it also suffices to etch the iron with dissolved salts or to use mixtures of salt and acid.

FIG. 1 shows a schematic side view of a device suitable for the purposes of the invention. The reduction can be carried out, for example, in the following way therewith:

Water, acid and nitro compound are charged into the device illustrated in FIG. 1 (mixing vessel 1) and thoroughly mixed with the stirrer 4. Water and ground cast iron filings are charged into the reaction vessel 2 with partially open ventilation 5 and kept in suspension by stirring vigorously with the stirrer 6. The iron suspension is warmed to a temperature of 70° to 80° C. The acid is introduced into the iron filings suspension, which is then warmed to 100° C. while stirring with the stirrer 6, and treated at this temperature with a portion of the nitro suspension or solution contained in the mixer vessel 1 by way of the pipe 7. When the reduction is complete, stirring is continued more slowly so that the non-oxidised iron filings can settle, and a portion, preferably 30 to 70%, of the reduction mixture (water+amino compound +$Fe_3O_4$), is forced by overpressure by introducing nitrogen through the pipe 8 or pumped by means of the pump 10 through the pipe 11 into the container 3.

After the pumping operation is complete, the reaction vessel is vented via the pipe 5. While stirring slowly with the stirrer 6, ground iron fillings and—depending on the pH value—acid are added to the residual reduction mixture via the filler inlet 9. Thereafter the vent 5 is closed, the rate of stirring is increased, and a second portion of the nitro suspension or solution is introduced through the pipe 7 from the mixing vessel 1. When the reduction is complete, working up is effected as described hereinbefore. The reduction cycle is repeated as often as required. The reduction mixtures forced with nitrogen or pumped with the pump 10 into the vessel 3 are further processed in known manner, i.e. $Na_2CO_3$ or NaOH is added thereto by small amounts at a temperature of 80° to 85° C. until a pH of 8.5 to 10.5 is attained, the alkaline suspension is freed from precipitated $Fe_3O_4$ and, if appropriate, sodium chloride is added to the amino suspension to precipitate the amino compound.

As is evident from what has been described hereinbefore, in the process of the present invention, in contrast to the conventional Béchamp process, the iron oxide, together with the dissolved amino compound and any impurities still present, is separated off without any change in the pH of the reaction mixture. A separation of iron oxide and impurites on the one hand, and of unconsumed iron on the other, is thereby achieved, this latter being directly available for the reduction of a further portion of nitro compound. The advantage of this method therefore lies in the very good utilisation of the iron employed. In contradistinction thereto, hitherto the reaction mixture was made alkaline and subsequently only the solution of the amine was separated off, so that iron oxide, unconsumed iron and impurities remained as solid residue. The iron contained in this residue was unsuitable for reuse, so that substantial losses of iron had to be tolerated. In addition on account of the iron filings present in the residue the filler cakes had to be dimensioned to an unnecessarily large degree.

In the process of the present invention, preferably one fifth to three fifths of the stoichiometric amount of nitro solution or suspension of the iron filings is introduced. The use of one fourth of the stoichiometric amount is particularly preferred. The amount of iron is then initially four times as great as the theoretical amount and the reaction proceeds correspondingly more vehemently to form the equivalent amount of oxide. After the reaction has subsided, stirring is continued and for example half of the resultant amino compound/iron oxide mixture is removed and further worked up in known manner. The residual iron is replenished with approximately the theoretical requirement of fresh iron, briefly etched, and treated with a further one fourth of the stoichiometric amount of nitro suspension or solution. Thereafter a portion, preferably half, of the contents of the vessel is again removed while stirring slowly, the iron replenished and one more etched with acid and treated with a fresh nitro suspension or solution etc.

The aqueous amino compound/iron oxide mixtures are worked up in known manner by adding sodium carbonate or sodium hydroxide solution and filtering off iron salt and, if appropriate, separating the resultant amine by salting it out.

The process of this invention makes it possible to obtain particularly pure amino compounds and, in addition, to increase the yields of amino compounds in respect of the iron employed.

By stoichiometric amount is meant the theoretical equivalent amount is meant the theoretical equivalent amount of Fe, in which connection it is known that 9/4 moles of iron are consumed per 1 mole of a mononitro compound, in accordance with the formula

$$4R-NO_2 + 9Fe + 4H_2O \rightarrow 4R-NH_2 + 3Fe_3O_4.$$

The following Examples illustrate the invention without restricting it to what is described therein.

EXAMPLE 1

(A) 300 g of water are charged into a first reaction vessel equipped with stirrer and 272 g of 100% nitrobenzenedisulphonic acid-2,5 are added with stirring. Stirring is continued until the pH is adjusted to 6 to 6.2

(B) 100 g of water are charged into a second reaction vessel equipped with stirrer and an outlet pipe and 100 g of ground cast iron filings are added with stirring. The batch is warmed to 80° C. with direct steam and at this temperature 5.6 g of acetic acid (100%) are introduced while warming to 100° C. with constant stirring. After a reaction time of 30 minutes, 330 g (=app. half) of the suspension contained in the first reaction vessel are added in the course of 30 minutes to the reaction mixture with very rapid stirring. Subsequently 180 g of the reaction mixture are forced with nitrogen into a third reaction vessel through the outlet pipe while stirring slowly.

(C) After this discharge, 60 g of cast iron filings are added to the second reaction vessel, with stirring, at pH 5. Thereafter the remaining 330 g of the suspension contained in the first reaction vessel are introduced at 100° C. in the course of 30 minutes and 180 g of the reaction mixture is removed as described in (B) etc.

(D) The reaction mixture discharged into the third reaction vessel is alkalised at on each occasion 85° C. with 15 g of 50% sodium hydroxide solution (pH 9), freed from residual iron oxide by filtration at 95° C., cooled, adjusted to pH 0.1 to 0.2 with 100 g of hydrochloric acid, treated with 130 g of sodium chloride and filtered. Yield: 100.6 g of aniline-disulphonic acid (100%) per reduction batch (in accordance with B). The yield of amino compound is 74% calculated on the nitrobenzenedisulphonic acid-2,5 used. Over a one week cycle, the consumption of cast iron filings is 64% of the amount of amine obtained.

EXAMPLE 2

(A) 500 g of water are charged into a first reaction vessel equipped with stirrer and then 4 g of 100% acetic acid and 117 g of 100% nitrophenolmethylsulphone-2,1,4 are added wet with stirring. Stirring is continued until the pH is adjusted to 3.5 to 4.2

(B) 80 g of water are charged into a second reaction vessel equipped with stirrer and an outlet pipe and 140 g of ground cast iron filings are added with stirring. The batch is warmed to 80° C. with direct steam and at this temperature 6 g of acetic acid (100%) are introduced while warming to 100° C. with constant stirring. After a reaction time of 30 minutes, 350 g (=app. half) of the suspension contained in the first reaction vessel are added in the course of 30 minutes to the reaction mixture with very rapid stirring. Subsequently 180 g of the reaction mixture are forced with nitrogen into a third reaction vessel through the outlet pipe while stirring slowly.

(C) After this discharge 30 g of cast iron filings and 1 to 2 g of 100% acetic acid are added to the second reaction vessel with stirring. Thereafter the remaining 350 g of the suspension contained in the first reaction vessel are introduced at 100° C. in the course of 30 minutes and 180 g of the reaction mixture is removed as described in (B) etc.

(D) The reaction mixture discharged into the third reaction vessel in accordance with (B) is alkalised on each occasion at 85° C. with 20 g of 50% sodium hydroxide solution. The batch is then stirred for 1 hour at 95° C. and subsequently freed from residual iron oxide at 95° C. by filtration and acidified with 90 g of 33% hydrochloric acid. The solution contains 45 g of aminophenolmethylsulphone-2,1,4 (100%) per reduction batch (in accordance with B). The yield of amino compound is 75% calculated on the nitrophenolmethylsulphone used. Over a one week cycle, the consumption of cast iron filings is 80% of the amount of amine obtained.

EXAMPLE 3

(A) 500 g of water are charged into a first reaction vessel equipped with stirrer and then 2.4 g of 100% acetic acid and 138.8 g of wet 100% 4,4'-dinitrostilbene-2,2'-disulphonic acid as sodium salt (molecular weight 430) are added with stirring. Stirring is continued until the pH is adjusted to 3.5 to 4.2.

(B) 80 g of water are charged into a second reaction vessel equipped with stirrer and an outlet pipe and 160 g of ground cast iron filings are added with stirring. The batch is warmed to 80° C. with direct steam and at this temperature 3 g of aqueous 50% sodium hydroxide solution and 4.8 g of acetic acid (100%) are introduced while warming to 100° C. with constant stirring. After a reaction time of 30 minutes, 330 g (=app. half) of the suspension contained in the first reaction vessel are added in the course of 30 minutes to the reaction mixture with very rapid stirring. Subsequently 180 g of the reaction mixture are forced with nitrogen into a third reaction vessel through the outlet pipe while stirring slowly.

(C) After this release, 40 g of cast iron filings, 1.5 g of 50% aqueous sodium hydroxide solution and 1.5 g of 100% acetic acid, which have to been mixed beforehand, are added to the second reaction vessel with stirring. Thereafter the remaining 370 g of the suspension contained in the first reaction vessel are introduced at 100° C. in the course of 30 minutes and 180 g of the reaction mixture is removed as described in (B) etc.

(D) The reaction mixture discharged into the third reaction vessel in accordance with (B) is neutralised on each occasion at 85° C. with 5 g of sodium carbonate, freed from residual iron oxide by filtration at 95° C., cooled, treated with 300 g of sodium chloride and filtered. Yield: 55.5 g of 4,4'-diamino-stilbene-2,2'-disulphonic acid (100%) per reduction batch (in accordance with B). The yield of diamino compound is 80%, referred to the 4,4'-dinitrostilbene-2,2'-disulphonic acid used. Over a one week cycle, the consumption of iron filings is 75% of the amount of diamine obtained.

EXAMPLE 4

(A) 250 g of water are charged into a first reaction vessel equipped with a stirrer and 112.9 g of 6-nitro-2-naphthol-4-sulphonic acid are added wet thereto with stirring. Stirring is continued until the pH is adjusted to 5.0 to 6.0. This pH value is corrected, if necessary, with acetic acid.

(B) 120 g of water are charged into a second reaction vessel equipped with a stirrer and a shortened outlet pipe and 180 g of ground cast iron filings are added thereto with stirring. Heating with direct steam is effected to a temperature of 80° C. and 14 g of 100% acetic acid are added while the batch is further heated with constant stirring to 100° C. After a reaction time of 30 minutes the suspension contained in the first reaction vessel is added with very rapid stirring to the reaction mixture in the course of app. 30 minutes. Thereafter app. 180 g of the reaction mixture are forced with nitrogen into a third reaction vessel through the outlet pipe while stirring slowly.

(C) After this discharge, the pH in the second reaction vessel is checked and adjusted to 5.0 to 5,5 with app. 5 g of acetic acid. A further 60 g of ground cast iron filings are subsequently added and a further suspension, which has been prepared as described in (A), is added at 100° C. in the course of 30 minutes. Then 180 g of the reaction mixture are discharged again as described in (B).

(D) The reaction mixture discharged as described in (B) is alkalised in the third reaction vessel at 85° C. on each occasion with app. 18 g of sodium carbonate (pH value=app. 8.5–9.0). The precipitated iron oxide mixture is collected hot by filtration and washed with hot water until a final volume of 900 ml is attained.

To isolate the amino compound, the pH is adjusted to 1.5 to 2.0 at 40° C. with app. 120 g of conc. hydrochloric acid and the batch is cooled to 20° C.

The precipitated compound is separated from the mother liquor by filtration. The yield is 100 g (=81.4%, referred to the nitro compound used). Over a one week cycle, the consumption of iron filings is app. 65% of the amount of amine obtained.

EXAMPLE 5

(A) 200 g of water are charged into a reaction vessel equipped with a stirrer and 71.3 g of 2-chloro-5-nitrobenzoic acid are added thereto with stirring.

Stirring is continued until the pH is adjusted to a value of 6.0 to 7.0, corrected with ammonia solution, if necessary. The mixture is thereafter warmed to 60° C.

(B) 120 g of water are charged into a second reaction vessel equipped with a stirrer and a shortened outlet pipe and 170 g of ground cast iron filings are added thereto with stirring. Heating with direct steam is effected to a temperature of 80° C. and 24 g of ammonium sulphate are added while the batch is further heated with constant stirring to 100° C. After a reaction time of 30 minutes the suspension contained in the first reaction vessel is added with very rapid stirring to the reaction mixture in the course of app. 30 minutes. Thereafter app. 180 g of the reaction mixture are forced with nitrogen into a third reaction vessel through the outlet pipe while stirring slowly.

(C) After this discharge, the pH in the second reaction vessel is checked and adjusted to 6.0 to 7.0 with app. 2 g of ammonium sulphate. A further 80 g of ground cast iron filings are subsequently added and a further suspension, which has been prepared as described in (A), is added at 100° C. in the course of 30 minutes. Then 180 g of the reaction mixture are discharged again as described in (B).

(D) The reaction mixture discharged as described in (B) is alkalised in the third reaction vessel at 85° C. on each occasion with app. 20 g of sodium carbonate (pH value=app. 8.5–9.0). The precipitated iron oxide mixture is collected hot by filtration and washed with hot water until a final volume of 600 ml is attained.

To isolate the amino compound, the pH is adjusted to 1.0 to 1.2 at 40° C. with app. 70 g of conc. sulphuric acid and the batch is cooled to 20° C.

The precipitated compound is separated from the mother liquor by filtration. The yield is 50 g (=70.1%, referred to the nitro compound used). Over a one week cycle, the consumption of iron filings is app. 160% of the amount of amine obtained.

We claim:

1. In a process for the production of a water-soluble aromatic amine compound by the reduction of a corresponding nitro compound selected from the group consisting of nitrobenzene, 2-nitro-4-methylsulphonylphenol, 2-nitro-2'-sulpho-4,4'-dichloro-diphenyl ether, 4,4'-dinitro-stilbene-2,2'-disulphonic acid, nitrobenzenedisulphonic acid-2,5,3-nitrobenzenesulphonic acid, 6-nitro-2-naphthol-4-sulphonic acid or 2-chloro-5-nitrobenzoic acid, with iron in acidic aqueous medium, the improvement comprising, a semi-continuous process comprising the steps of (1) providing an aqueous solution or suspension of the aromatic nitro compound in a first vessel, (2) providing an acidic aqueous suspension of iron particles in a second vessel, (3) introducing a less-than-stoichiometric amount of the suspension of the aromatic nitro compound from the first vessel into the second vessel, (4) allowing the acidic suspension of iron to react with the aromatic nitro compound to yield to aromatic amine compound and iron oxide, at about 50° C. to about 110° C., (5) substantially separating the unreacted iron particles from the reaction mixture by removal of a substantial portion of the iron oxide, water and aromatic amine compound from the second vessel, while leaving the unreacted iron particles therein, (6) repeating steps (3), (4) and (5) while maintaining the acidity and the stoichiometric excess of unreacted iron in the reaction mixture.

2. The process of claim 1, wherein the substantial portion of iron oxide, water and aromatic amine compound removed from the second vessel in step (5) is about 30% to about 70% of that present in the reaction mixture.

3. The process of claim 1, wherein the aromatic amine compound is soluble under the reaction conditions in the reaction medium.

4. The process of claim 1, wherein the reaction is carried out at a temperature in the range of about 90° C. to about 100° C.

5. The process of claim 1, wherein the less-than-stoichiometric amount of the suspension of the aromatic nitro compound in step (3) is about 1-fifth to about 3-fifths of the stoichiometric amount.

6. The process of claim 1, wherein the acid of the acidic aqueous suspension of iron particles is acetic acid.

7. The process of claim 1, wherein the aromatic nitro compound is 4,4'-dinitrostilbene-2,2'-disulfonic acid.

8. The process of claim 1, further comprising the steps of alkalizing the separated portion of iron oxide, water and aromatic amine, for step (5), removing the iron oxide by filtration, and precipitating the aromatic amine compound from the filtrate.

* * * * *